United States Patent [19]

Ishida

[11] 4,352,988
[45] Oct. 5, 1982

[54] APPARATUS FOR DISCRIMINATING SHEETS

[75] Inventor: Tsuyoshi Ishida, Yokohama, Japan

[73] Assignee: Tokyo Shibaura Denki Kabushiki Kaisha, Kawasaki, Japan

[21] Appl. No.: 206,894

[22] Filed: Nov. 14, 1980

[30] Foreign Application Priority Data

Nov. 22, 1979 [JP] Japan ................................ 54-150603

[51] Int. Cl.³ .......................................... G01N 21/86
[52] U.S. Cl. ................................... 250/559; 356/435
[58] Field of Search ............... 250/556, 559, 562, 563, 250/571, 572, 223 R; 356/434, 435, 444, 448

[56] References Cited

U.S. PATENT DOCUMENTS 3,448,279 6/1969 Lindemann et al. ................ 250/562
3,922,557 11/1975 Carnes .................................. 250/571
4,284,356 8/1981 Heilman .............................. 250/559

*Primary Examiner*—David C. Nelms
*Attorney, Agent, or Firm*—Cushman, Darby & Cushman

[57] ABSTRACT

A sheet discriminating apparatus comprises, in addition to a first detecting system for detecting light transmitted through a sheet and a second detecting system for detecting light reflected by the front surface of the sheet, a third detecting system for detecting light reflected by the rear surface of the sheet. The light doses sensed by these detecting systems are integrated by respective integrators for a predetermined period of time, and the outputs obtained from the integrators are coupled to an adder and added together therein. The sum output of the adder and a reference signal generator are compared with each other in a comparator, and the determination as to whether the sheet in question is adequate for re-use or not is effected on the basis of the result of the comparison.

10 Claims, 6 Drawing Figures

APPARATUS FOR DISCRIMINATING SHEETS

This invention relates to apparatus for sorting sheets such as bank notes into effective sheets and rejected sheets through automatic discrimination and, more particularly, to apparatus for discriminating adequate and inadequate sheets through detection of overall contamination of sheet.

Recently, various sheet sorting apparatus for sorting sheets such as bank notes and securities into valid sheets and rejected sheets through automatic discrimination have been developed and put to practical use.

In this type of sheet sorting apparatus, while the sheets loaded are counted to check for excess and deficiency, those sheets which are incapable of sorting, for instance different kinds of sheets and ineffective notes, are removed as rejected sheets, and also the effective sheets are sorted into damaged sheets (which are inadequate for re-use although they are valid) and sound sheets (adequate for re-use), the sorted sheets being bundled into bundles each consisting of, for instance, 100 sheets, which are then stamped.

FIG. 1 shows the construction of a typical sheet sorting apparatus of this type. It comprises a supply section 100, a take-out and transfer section 200, a discriminating section 300, a sorting section 400, a sorted sheet collecting section 500 and a bundling section 600. A number of sheet bundles are loaded in the supply section 100 and are supplied one after another to the take-out and transfer section 200. In the take-out and transfer section 200, notes P supplied from the supply section 100 are take out one after another by vacuum attraction to be transferred to the discriminating section 300. In the discriminating section 300, necessary discrimination of the notes P taken out and transferred by the take-out and transfer section 200 is made. In the sorting section 400, the notes P having been taken out and transferred by the take-out and transfer section 200 and passed through the discriminating section 300 are sorted on the basis of the result of discrimination in the discriminating section 300 and transferred to the collecting section 500. In the section 500, the proper notes transferred from the sorting section 400 are stacked substantially in a horizontal state and transferred as stacks each consisting of 100 notes to the bundling section 600. In the bundling section 600, the sheet stacks consisting of 100 sheets, supplied one after another from the section 500, are successively bundled, the bundles thus produced being transferred to the outside of the apparatus. In such sorting apparatus, the discriminating section 300 consists of an optical discriminating section, a magnetic discriminating section and a mechanical discriminating section, and the invention appertains to the optical discriminating section. FIG. 2 shows a typical construction of the optical discriminating section. In this section, each sheet P transferred from the take-out and transfer section 200 is entirely irradiated by light from a light source 10 transmitted through a lens 12 and incident in a direction at right angles to the direction of transfer of the sheet P. The reflected light is focused through a condensing lens 14 on a slit plate 16. Light transmitted through the slit plate 16 is dispersed through a dispersing box 18 to be incident on a photoelectric element 20.

Meanwhile, light transmitted through the sheet is dispersed through a dispersing box 22 to be incident upon a photoelectric element 24. The outputs of the photoelectric elements 20 and 24 are coupled through respective amplifiers 26 and 28 to respective integrators 30 and 32. A detector 34 consisting of a light source 36 and a photoelectric element 38 detects passage of sheet. The output signal from the detector 34 is coupled to a control circuit 40. The control circuit 40 produces control signals for starting and ending integration so that integration may be effected for a predetermined period of time in the integrators 30 and 32. The output signals from the integrators 30 and 32, produced as a result of integration, are coupled to respective comparators 42 and 44 at one of its input terminals thereof.

To the other input terminal of each of the comparators 42 and 44 is coupled a reference signal for determination produced from a reference signal generator 46 including a pull-up resistor 48, a zener diode 50 and a variable resistor 52, whereby whether the sheet in question is adequate for re-use or not is determined.

When discriminating whether or not a sheet is adequate from light transmitted through it, the more the sheet is contaminated the less light is transmitted provided the thickness of the sheets P is the same. However, the thickness of sheets actually vary considerably, and thus it is likely that a comparatively thick sheet is erroneously determined to be an inadequate sheet from less transmitted light. In addition, when discriminating whether a sheet is adequate or inadequate, with a new sheet P the light reflected from the entire sheet is sometimes unexpectedly less because of high density of printed ink. Therefore, there is a possibility that a bland new sheet is erroneously determined to be a contaminated sheet.

As a prior-art, Japanese Utility Model Publication No. 50-25195 discloses an apparatus, in which bank notes being moved with the rotation of a transparent cylinder are sorted on the basis of light beam transmitted through the cylinder. However, there is no disclosure concerning the treatment of electric signal produced as a result of the incidence of the transmitted light on a photoelectric element.

The primary object of the invention is to provide an improved sheet discriminating apparatus.

Another object of the invention is to provide a sheet discriminating apparatus, which comprises, in addition to the first detecting system for detecting light reflected by the front surface of sheets and the second detecting system for detecting light transmitted through sheets, a third detecting system for detecting light reflected by the rear surface of sheets.

A further object of the invention is to provide a sheet discriminating apparatus, in which light reflected by the front and rear surfaces of sheet and light transmitted through the sheet are filtered through optical filters.

A still further object of the invention is to provide a sheet discriminating apparatus, in which the sum of values obtained as a result of integration of light reflected from the front and rear surfaces of sheet and a value obtained as a result of integration of light transmitted through the sheet is taken.

A yet further object of the invention is to provide a sheet discriminating apparatus, in which the light dose ratio between light reflected by the front surface of sheet and light transmitted therethrough and also the light dose ratio between light reflected by the rear surface of sheet and light transmitted therethrough are variable.

To achieve the above objects, the sheet sorting apparatus according to the invention comprises a reference signal generator, a first detecting system for detecting light transmitted through a sheet, a second detecting system for detecting light reflected by the front surface of the sheet, a third detecting system for detecting light reflected by the rear surface of the sheet, a detector for detecting the passage of the sheet therethrough, first to third amplifiers for amplifying the outputs of the respective first to third detecting systems, first to third integrators for integrating the outputs of the first to third amplifiers, a control circuit for supplying a signal concerning the integration period to each of the first to third integrators in accordance with a detection signal produced from the detector, an adder for taking the sum of the output signals from the first to third integrators, and a comparator for comparing the output signal coupled as one of two inputs from the adder and the output signal coupled as the other input from the reference signal generator, thereby effecting the determination as to whether or not the sheet in question is adequate.

The above and other objects and features of the present invention will be more apparent from the following description taken in connection with the accompanying drawings.

FIG. 6 is a schematic showing a modification of the embodiment of FIG. 5.

Figure 1:
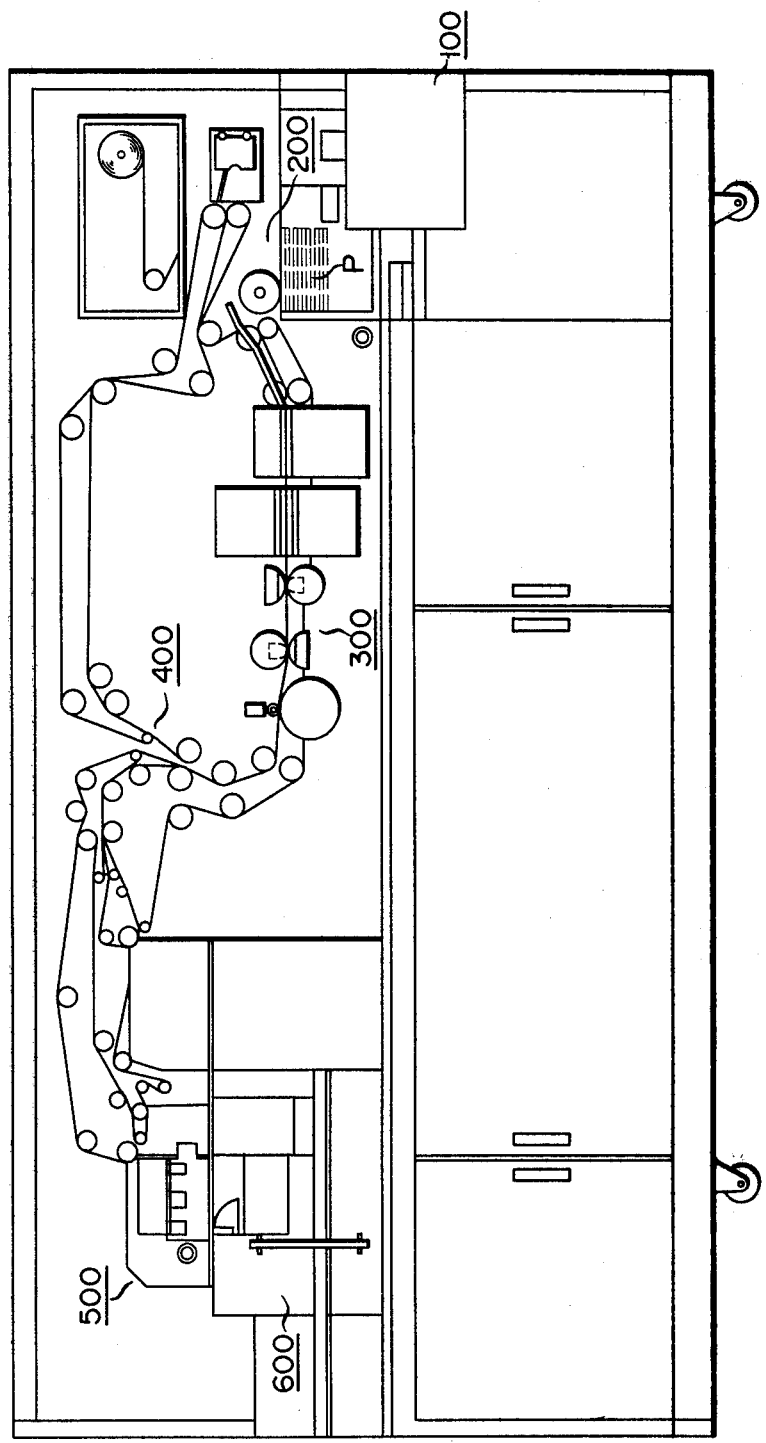
FIG. 1 is a schematic view showing a sheet sorting apparatus incorporating a prior-art sheet discriminating apparatus.
Figure 2:
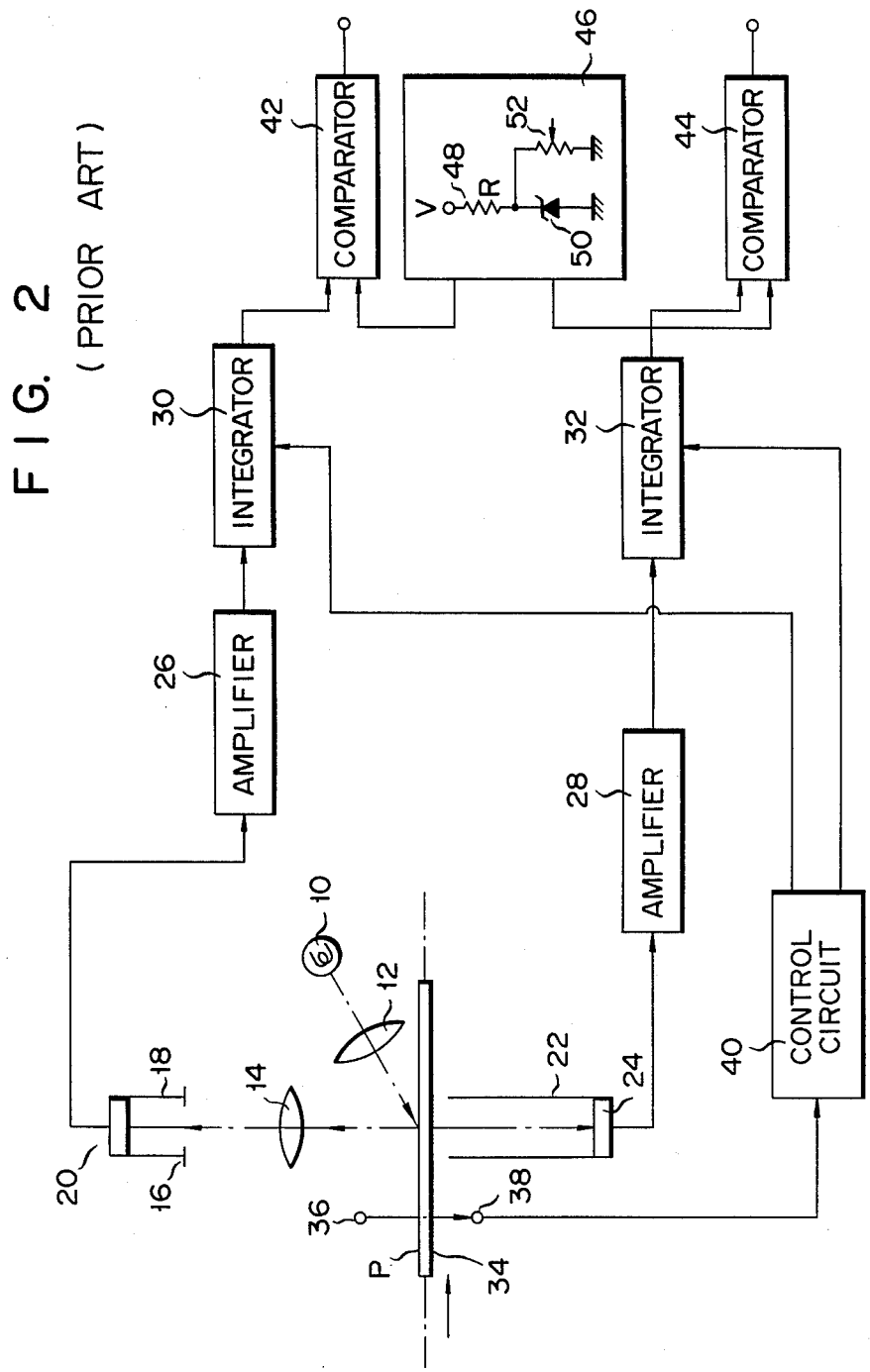
FIG. 2 is a schematic representation of a prior-art sheet sorting apparatus.
Figure 3:
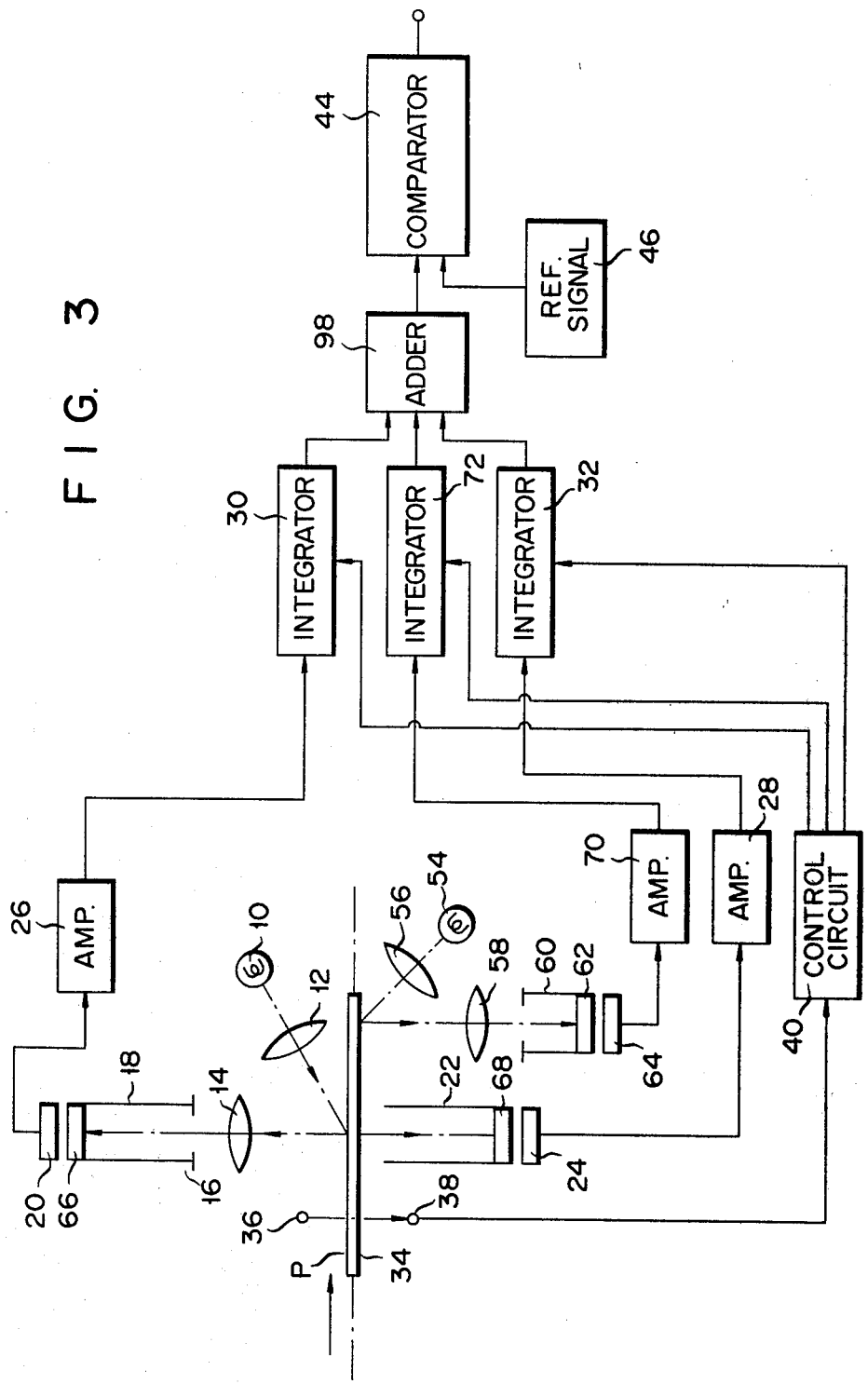
FIG. 3 is a schematic representation of one embodiment of the sheet sorting apparatus according to the invention.

FIG. 3 shows a schematic representation of an embodiment of the invention. In the Figure, the corresponding parts to those in FIG. 2 are designated by like reference numerals, and their detailed description is omitted. One feature of the invention resides in the provision of a third detecting system for detecting light reflected by the rear surface of sheets. The third detecting system includes a light source 54, a lens 56, a condensing lens 58, a dispersing box 60, an optical filter 62 and a photoelectric element 64. The optical filter 62 is provided with a characteristic conforming to the sense of viewing of the eye. This means that the determination as to whether the sheet P is contaminated or not is made with the sense of viewing of the eye. In this case, the difference between an old sheet and a bland new sheet is pronounced in blue and green portions, and the filter is made to have such a characteristic that it mainly passes blue and green components of light. In this embodiment, the first detecting system for detecting light reflected by the front surface of sheets and the second detecting system for detecting light transmitted through sheets are provided with respective optical filters 66 and 68.

The output signals from the first to third detecting systems, produced as a result of photoelectric conversion, are coupled to the first to third amplifiers 26, 28 and 70. These amplifiers 26, 28 and 70 amplify respective input signals, i.e., signals obtained as a result of photoelectric conversion of light reflected by the front surface of a sheet, light transmitted through the sheet and light reflected by the rear surface of the sheet, and their outputs are coupled to respective integrators 30, 32 and 72. An integration period signal is supplied from control circuit 40 to the integrators 30, 32 and 72 so that integration is made therein for a predetermined period of time.

Figure 4:
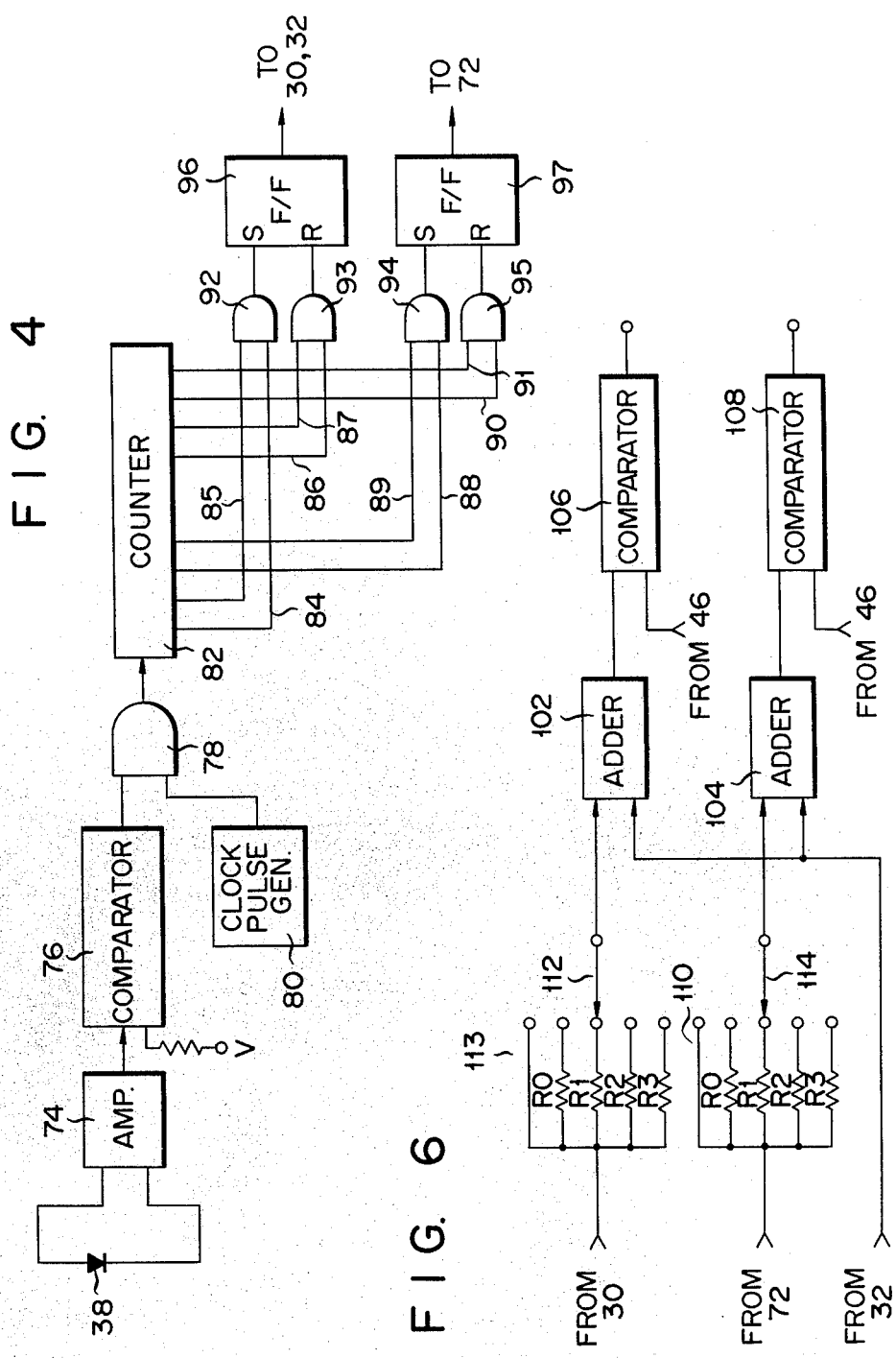
FIG. 4 is a schematic showing the detailed construction of the control circuit shown in FIG. 4.

FIG. 4 shows an example of the construction of the control circuit 40. The signal from light receiving element 38 in detector 34 as mentioned above is amplified by an amplifier 74 and then compared in a comparator 76 with a reference signal level for conversion into a digital value. This digital value signal is coupled in synchronism to a reference clock signal from a clock pulse generator 80 through an AND gate 78 to a binary counter 82.

The binary counter 82 produces binary value outputs 84 to 91 coupled through first to fourth AND gates 92 to 95 to first and second flip-flops 96 and 97. More particularly, the binary value outputs 84 and 85 are supplied as set signal to the first flip-flop 96, the outputs 86 and 87 are supplied as reset signal to the flip-flop 96, the outputs 88 and 89 are supplied as set signal to the second flip-flop 97, and the outputs 90 and 91 are supplied as reset signal to the flip-flop 97.

The first flip-flop 96 thus supplies an integration start signal and an integration end signal to the first and second integrators 30 and 32, and the second flip-flop 97 supplies an integration start signal and an integration end signal to the third integrator 72.

Referring to FIG. 3 again, the output signals from the first to third integrators 30, 32 and 72 are coupled to an adder 98 and added together therein. The resultant sum is coupled to one of two input terminals of a comparator 44. A reference signal from a reference signal generator 46 is supplied to the other input terminal of the comparator 44, and determination as to whether the sheet in question is adequate or not is made according to the result of comparison of the sum output from the adder 98 and the reference signal.

With the above sheet discriminating apparatus according to the invention, a comparatively thick sheet P adequate for re-use, which is deemed to be erroneously determined to be an inadequate sheet with the prior-art discriminating apparatus due to less light transmitted through it, will not be determined to be inadequate because of much light reflected by its front and rear surfaces. Also, a bland new sheet P, with which the density of printed ink is high so that less light is reflected, will not be erroneously determined to be an inadequate sheet since much light is transmitted.

Figure 5:
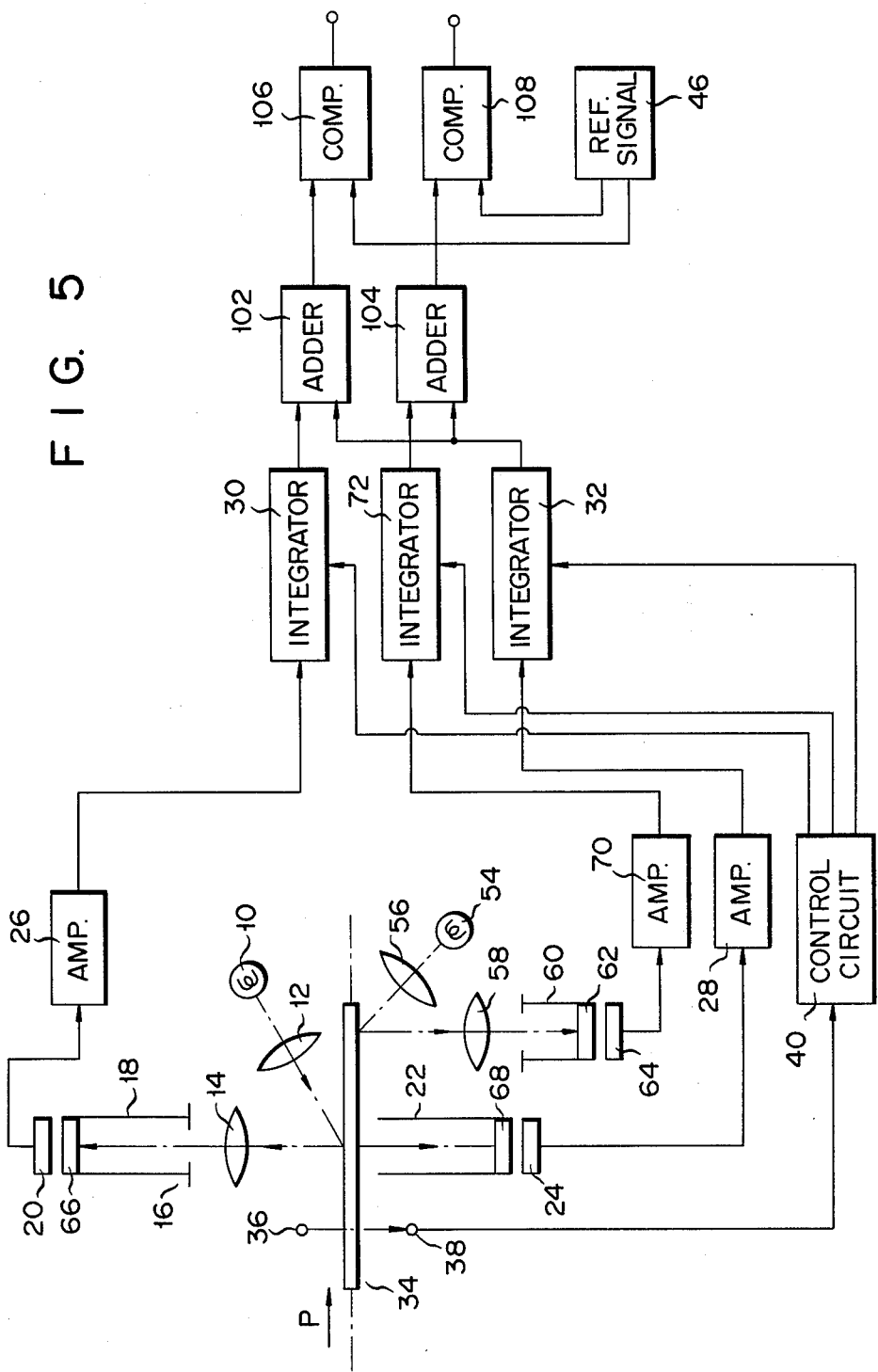
FIG. 5 is a schematic representation of another embodiment of the invention.

FIG. 5 shows a different embodiment of the invention. In the Figure, the corresponding parts to those in FIG. 3 are designated by like reference numerals, and their detailed description is omitted. A feature of this embodiment is that the sum of light reflected by the front surface of a sheet and light transmitted therethrough and the sum of light reflected by the rear surface of the sheet and light transmitted therethrough are separately obtained and compared with respective reference signals. More particularly, the outputs of first and second integrators 30 and 32 are coupled to a first adder 102, and the outputs of second and third integrators 32 and 72 are coupled to a second adder 104. The first adder 102 supplies an output, which represents the sum of light reflected by the front surface of a sheet and light transmitted therethrough, to a first comparator 106. The second adder 104 supplies an output, which represents the sum of light reflected from the rear surface of the sheet and light transmitted therethrough, to a second comparator 108. A reference signal is supplied from reference signal generator 46 to each of the first and second comparators 106 and 108 for comparison therein. Whether the sheet is adequate for re-use or not is determined on the basis of the results of the comparisons.

FIG. 6 shows a modification of the embodiment shown in FIG. 5. In this example, a first light dose ratio setting circuit 113 for setting the light dose ratio between light reflected by the front surface of sheet and light transmitted therethrough and a second light dose setting circuit 110 for setting the light dose ratio between light reflected by the rear surface of sheet and light transmitted therethrough are provided. The first light dose ratio setting circuit 113 is provided between the first integrator 30 and first adder 102, and the second light dose ratio setting circuit 110 is provided between the third integrator 72 and second adder 104. These light dose ratio setting circuits 113 and 110 consist of respective resistor networks, the resistance values of which are selected by respective switches 112 and 114. While the ratio between transmitted light and reflected light is usually 1:1, when there are fluctuations of some sort or other in the sheets that are dealt with, the ratio has to be adjusted to an optimum value. Table 1 below shows ratios between transmitted light and reflected light to be selected for various cases where there are fluctuations, these data being obtained as a result of experiments conducted by the inventor.

TABLE 1

| Sheet | Transmitted light | Reflected light |
| --- | --- | --- |
| Fluctuations in thickness | Small dose | Large dose |
| Dark color ink | Large dose | Small dose |
| Bright color ink | Medium dose | Medium dose |
| Fluctuations in ink density | Large dose | Small dose |

With the above construction, the ratio between light reflected by the front surface of sheet and transmitted therethrough and the ratio between light reflected by the rear surface of sheet and light transmitted therethrough can be adjusted to an optimum value conforming to the kind of sheets that are dealt with.

What is claimed is:

1. An apparatus for discriminating sheets being transferred into adequate and inadequate sheets through detection of contamination of these sheets, comprising:
   a reference signal generator;
   a first detecting system for detecting light transmitted through said sheets;
   a second detecting system for detecting light reflected by the front surface of said sheets;
   a third detecting system for detecting light reflected by the rear surface of said sheets;
   a detector for detecting the passage of each of said sheets therethrough;
   first to third amplifiers for amplifying the outputs of said respective first to third detecting systems;
   first to third integrators for integrating the outputs of said respective first to third amplifiers;
   a control circuit for supplying an integration period signal to each of said first to third integrators according to a detection signal produced from said detector;
   an adder for taking the sum of the output signals from said first to third integrators; and
   a comparator for comparing the output signal coupled as one of two inputs from said adder and the output signal coupled as the other input from said reference signal generator thereby effecting the determination as to whether or not the sheet in question is adequate.

2. An apparatus for discriminating sheets being transferred into adequate and inadequate sheets through detection of contamination of these sheets, comprising:
   a reference signal generator;
   a first detecting system for detecting light transmitted through said sheets;
   a second detecting system for detecting light reflected by the front surface of said sheets;
   a third detecting system for detecting light reflected by the rear surface of said sheets;
   a detector for detecting the passage of each of said sheets therethrough;
   first to third amplifiers for amplifying the outputs of said respective first to third detecting systems;
   first to third integrators for integrating the outputs of said respective first to third amplifiers;
   a control circuit for supplying an integration period signal to each of said first to third integrators according to a detection signal produced from said detector;
   first and second adders connected to said first to third integrators such that said first adder takes the sum of light reflected by the front surface of each of said sheets and light transmitted therethrough and said second adder takes the sum of light reflected by the rear surface of the sheet and light transmitted therethrough; and
   a comparator for comparing the output signal coupled as an input from said first or second adder and the output signal coupled as another input from said reference signal generator, thereby effecting the determination as to whether or not the sheet in question is adequate.

3. An apparatus for discriminating sheets according to claim 1 or 2, wherein said second detecting system includes:
   a light source;
   a lens for transmitting light from said light source to the front surface of each said sheet;
   a lens for condensing light reflected by the front surface of each said sheet;
   a slit plate for receiving said condensed light;
   a dispersing box for dispersing said received light; and
   a photoelectric converter element for photoelectrically converting said dispersed light.

4. An apparatus for discriminating sheets according to claim 1 or 2, wherein said third detecting system includes:
   a light source;
   a lens for transmitting light from said light source to the rear surface of each said sheet;
   a lens for condensing light reflected from the rear surface of each said sheet;
   a slit plate for receiving said condensed light;
   a dispersing box for dispersing said received light; and
   a photoelectric converter element for photoelectrically converting said dispersed light.

5. An apparatus for discriminating sheets according to claim 1 or 2, wherein said first detecting system includes:

a slit plate for receiving light incident upon the front surface of each said sheet and transmitted therethrough;

a dispersing box for dispersing said received light; and a photoelectric converter element for photoelectrically converting said dispersed light.

6. An apparatus for discriminating sheets according to claim 1 or 2, wherein said detector includes:

a light source disposed to be found on one side of each said sheet; and a photoelectric converter element disposed to be found on the other side of each said sheet.

7. An apparatus for discriminating sheets according to claim 1 or 2, wherein said control circuit includes:

an amplifier for amplifying the output of said detector for detecting the passage of each said sheet;

a comparator for converting the output signal from said amplifier into a digital value signal;

a gate circuit for passing said digital value signal from said comparator in synchronism to a reference clock pulse;

a clock pulse generator for generating said clock pulse;

a counter circuit for counting the output from said gate circuit to produce various count value signals; and first and second flip-flops for receiving count value signals from said counter circuit through gate circuits and supplying set and reset signals as respective integration start and end commands to said integrators.

8. An apparatus for discriminating sheets according to claim 1 or 2, which further comprises a light dose ratio setting circuit provided between said integrators on one hand and said adder or adders on the other hand such as to permit the ratio between the light dose sensed by said first detecting system and light dose sensed by said second detecting system and/or the ratio between the light dose sensed by said first detecting system and light dose sensed by said third detecting system to be varied before the summation of the light doses sensed by said first and second detecting systems and/or the summation of the light doses sensed by said first and third detecting systems are effected.

9. An apparatus for discriminating sheets according to claim 8, wherein said light dose ratio setting circuit is a resistor network, with the resistance thereof being capable of being selected by a switch.

10. An apparatus for discriminating sheets according to claim 3, 4 or 5, which further comprises optical filter means for filtering said dispersed light before said dispersed light is coupled to each of said photoelectric converter elements, said optical filter means having a characteristic conforming to the sense of viewing of the eye.

* * * * *